US005105801A

United States Patent [19]

Cathignol et al.

[11] Patent Number: 5,105,801

[45] Date of Patent: Apr. 21, 1992

[54] METHOD AND APPARATUS FOR IMPROVING THE REPRODUCIBILITY AND EFFICIENCY OF THE PRESSURE WAVES GENERATED BY A SHOCK WAVE GENERATING APPARATUS

[75] Inventors: Dominique Cathignol, Genas; Jean-Louis Mestas, Chassieu; Paul Dancer, Saint-Etienne; Maurice Bourlion, Saint-Chamond, all of France

[73] Assignees: Technomed International; INSERM, both of Paris, France

[21] Appl. No.: 742,097

[22] Filed: Aug. 2, 1991

Related U.S. Application Data

[63] Continuation of Ser. No. 545,519, Jun. 28, 1990, abandoned.

[30] Foreign Application Priority Data

Jun. 30, 1989 [FR] France .............................. 89 08846

[51] Int. Cl.[5] .............................................. A61B 17/22

[52] U.S. Cl. ............................... 128/24 FL; 367/147; 181/118

[58] Field of Search ........................ 367/147; 181/118; 128/24 EL; 72/56; 606/118

[56] References Cited

U.S. PATENT DOCUMENTS

| | | | |
|---|---|---|---|
| 2,559,227 | 7/1951 | Reiber . | |
| 3,559,435 | 2/1971 | Gerber . | |
| 4,610,249 | 9/1986 | Makofski | 128/24 EL |
| 4,651,311 | 3/1987 | Owen | 367/147 |

OTHER PUBLICATIONS

Dorsey, Properties of Ordinary Water Substances, Reinhold Pub. Co., 1940, pp. 380–381.

*Primary Examiner*—Francis Jaworski
*Assistant Examiner*—Scott R. Akers
*Attorney, Agent, or Firm*—Cohen, Pontani, Lieberman & Pavane

[57] ABSTRACT

The present invention relates to a method and device for discharging an electric current between two electrodes, comprising considerably reducing the resistance to the passage of electric current at least between the electrodes so as to bring it to a resistance value near to or slightly higher than the critical resistance by interposing a conductive electrolyte between electrodes. This improves the rate of discharge of an electric current produced between the electrodes, by eliminating substantially completely the latency time.

21 Claims, 2 Drawing Sheets

FIG. 2
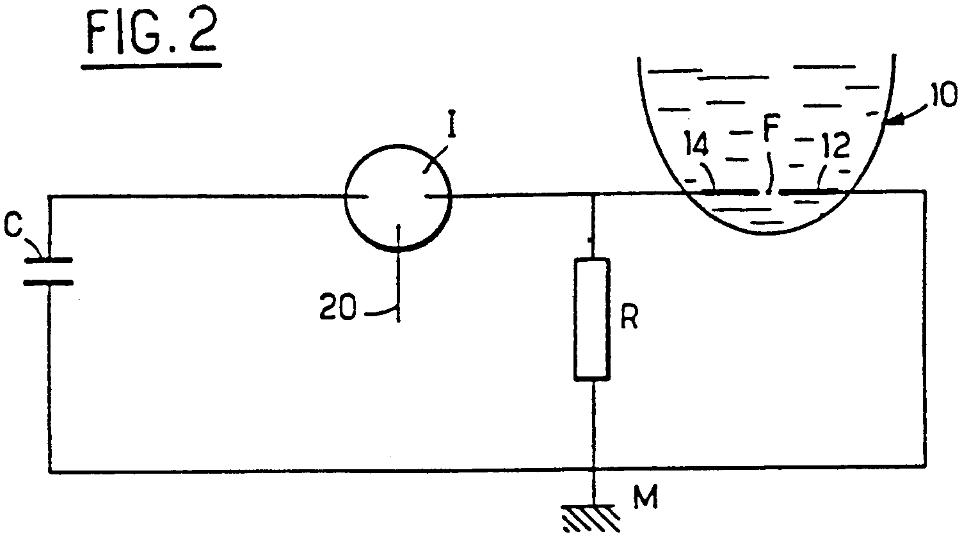
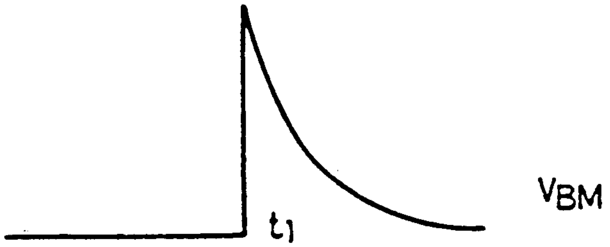
FIG. 3a
INVENTION
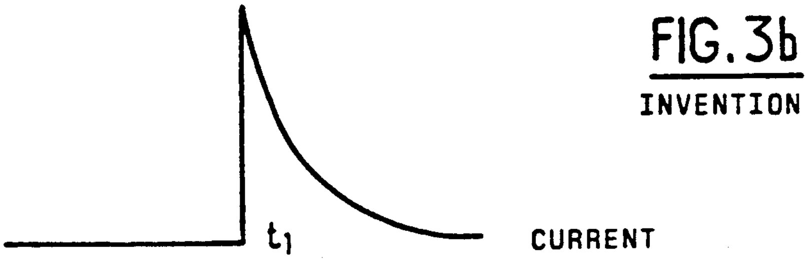
FIG. 3b
INVENTION
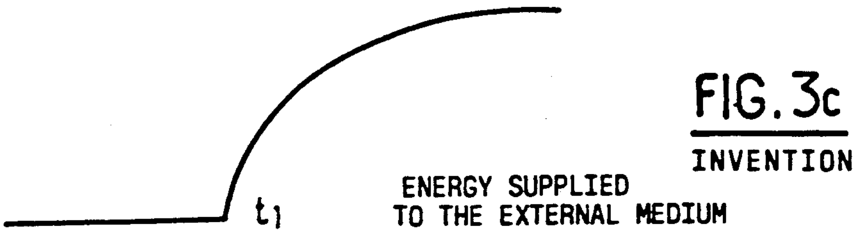
FIG. 3c
INVENTION

METHOD AND APPARATUS FOR IMPROVING THE REPRODUCIBILITY AND EFFICIENCY OF THE PRESSURE WAVES GENERATED BY A SHOCK WAVE GENERATING APPARATUS

This is a continuation of U.S. application Ser. No. 07/545,519, filed Jun. 28, 1990, now abandoned.

FIELD OF THE INVENTION

The invention essentially relates to a method and device for improving in particular the reproducibility and efficiency of pressure waves generated during the electric discharge from a capacitance between two electrodes, by interposition of an electrically conductive liquid between the electrodes, and a shockwave generating apparatus using such a method or device, particularly for hydraulic lithotripsy.

BACKGROUND OF THE INVENTION

An apparatus is known from U.S. Pat. No. 2,559,227 of RIEBER, for generating high frequency shockwaves, which apparatus comprises a truncated ellipsoidal reflector 80 in which shockwaves are generated by discharge or electric arc between two electrodes converging to the first focal point of the ellipsoid, the object being to destroy a target situated in the second focal point of the ellipsoid, which is external to the truncated reflector 80 (see FIG. 3 and col. 7, line 51, to col. 9, line 30).

Electrodes 12 and 13 are produced in a highly conductive material such as copper or brass and are mounted on an insulator 26 which is supported in pivotal manner by means of a device 11*a*, 11*b*, so as to adjust the spacing between said electrodes (see col. 4, lines 42 to 53 and col. 8, lines 40 to 47).

With the RIEBER apparatus or any similar apparatus, the discharge or electric arc is produced between the electrodes due to the sudden discharge of a capacitor 11, by closing a high voltage switch (see FIG. 2B). According to the RIEBER apparatus, the circuit between the electrodes comprises a capacitor, with an associated self-inductance. It has been noted that the capacitor discharge is of damped oscillatory type. In other words, the capacitor is going to discharge and to re-charge in reverse at a lower voltage than the initial voltage which is very high, until depletion of the charges contained in the capacitor occurs.

Simultaneously, an electric arc and a plasma are established between the two electrodes of which the current will also be, by way of consequence, of damped oscillatory type, as can be understood with reference to FIGS. 1*a*, 1*b* and 1*c* of the present application which illustrates prior art. Accordingly, FIG. 1*a* illustrates the chronogram of voltages, while FIG. 1*b* illustrates the chronogram of currents established in the RIEBER type discharge circuit. It is found that when the circuit is closed at time $t_1$, the voltage at the terminals of the electrodes rises suddenly to the value of the voltage at the terminals of the capacitors (see FIG. 1*a*). A low current is established between the two electrodes (FIG. 1*b*) due to the fact that, first the liquid in which the electrodes are immersed, and which is usually water, is still slightly electrically conductive, and second, that for reasons of safety and of arc ignition, a high resistance is provided in parallel to the capacitor supplying the electrodes.

After a certain time, namely after time $t_2$, called latency time, the arc is established between the electrodes. At that moment, the current increases suddenly by several KA as is clearly illustrated in FIG. 1*b*. It is a known fact that the arc is constituted by a plasma whose resistance is extremely low (about 1/100 or 1/1000 Ohm) and it is the low value of this resistance which explains the importance of the oscillations of current (FIG. 1*b*) and of voltage (FIG. 1*a*) during the discharge of a capacitor in an RL type circuit.

The energy contained and dissipated by the arc contributes to the vaporization of the liquid in which the electrodes are immersed, and which is normally water, to the creation of a steam bubble and consequently to the formation of the shockwave. The quicker this energy is dissipated, the more efficient will be the shockwave.

It is thus found that, due to the oscillatory nature of the current, as illustrated in FIG. 1*b*, the supply of energy to the external medium is progressive, as clearly illustrated in FIG. 1*c*.

This explains how, the quicker the vaporization of the liquid is, the stronger the pressure wave will be and it will have a shorter rising time.

Thus, a great quantity of energy will have to be delivered to vaporize quantity of energy will have to be delivered to vaporize a sufficient quantity of liquid, and in particular water.

Yet, virtually all the currently known devices use discharges which are all of damped oscillatory type, as illustrated in FIGS. 1*a* and 1*b*, resulting in a progressive dissipation of the energy with time (FIG. 1*c*)

In commonly assigned EP-A-0 296 912 which is equivalent to U.S. Pat. No. 4,962,753, a first solution has been prepared for delivering suddenly or in a relatively short time, most of the energy stored by the charge of the capacitor of the discharge circuit between two electrodes. It was proposed to this effect, to increase the electric resistance on the path of the electric arc at least between the electrodes by interposition of a high resistance insulating element (32), between the arc-generating electrodes 12, 14. This solution is fully satisfactory when generating shockwaves whose initial pressure wave is substantially spherical.

However, said prior solution is difficult to implement mechanically because of the small dimensions of the electrodes and of the mechanical strength towards shockwaves. Moreover, the latency time problem is not solved in that the main aim of this particular solution is only to improve the discharge rate when this is established, which does not improve the reproducibility of the discharge, nor consequently the reproducibility and efficiency of the generated pressure waves, nor does it reduce the wear of the electrodes.

U.S. Pat. No. 3,559,435 of GERBER describes the use of a conductive liquid to provide a preferential conductive pathway for the current in order to form an arc where the current is established (see col. 5, line 4). The object is therefore to establish an arc and a growth of plasma between two electrodes in a conventional discharge. The aim of the recommended electrolyte is therefore to establish a preferential current between the electrodes in order to create a high conductive plasma (col. 1, line 55).

GERBER's solution does not in any way alter the configuration of the oscillating current which causes the wear of the electrode, or of a progressive supply of the energy to the external medium.

SUMMARY OF THE INVENTION

The object of the present invention, on the contrary, is to prevent the appearance of any discharge oscillation. hence to prevent the formation of arc or plasma, and to supply the energy to the external medium between the electrodes in a very short time.

Accordingly, the main object of the invention is to solve the new technical problem which consists of providing a solution permitting instant delivery in a relatively short time of most of the energy stored by the charge of the capacitor of the discharge circuit between two electrodes, by eliminating substantially completely the latency time normally necessary for generating an electric discharge between the electrodes.

Another object of the invention is to solve the new technical problem consisting in providing a solution permitting substantially complete elimination of the latency time when generating an electric discharge between two electrodes while considerably improving the reproducibility and efficiency of the pressure waves generated during the discharge, notably due to an important improvement in localizing the generation of the discharge current, hence of the generated steam bubble.

Yet another object of the present invention is to solve the new technical problem consisting in providing a solution permitting substantially complete elimination of the latency time when generating an electric discharge between the electrodes, while producing a discharge a critically damped type which will cause instantaneous delivery, or a delivery in a relatively short time of most of the energy stored by the charge of the capacitor of the discharge circuit between the electrodes, thereby preventing the oscillations associated with the formation of the electric arc.

A further object of the present invention is to solve said new technical problems while providing a solution permitting a reduction of the wear of the electrodes.

Yet another object of the invention is to solve the aforesaid new technical problems in an extremely simple manner which can be used on an industrial scale, particularly with reference to apparatuses for extracorporeal destruction of concretions by using pressure waves (kidney lithiases, cholelithiases, and urinary (calculi) or of tissues (such as tumors) or for treating bone fractures.

All said new technical problems have been solved for the first time by the present invention in a satisfactory manner, for little costs, and at industrial level.

Thus, a first aspect of the present invention provides a method for improving the electric discharge rate produced in a liquid medium such as water, between at least two discharge electrodes, which process consists of considerably reducing the resistance to the passage of the current at least between the electrodes in order to bring it to a resistance value the critical resistance.

According to a particularly preferred embodiment of the present invention, said electrical resistance is reduced by using an electrically conductive liquid medium which is interposed at least between the electrodes.

According to a particularly advantageous embodiment of the present invention, the electrically conductive liquid medium used as an electrical resistance which is at least 1/10, and preferably at least 1/100 of the electrical resistance value of the normally ionized water used as a reference. Preferably still, the electrical resistance of the electrically conducting medium according to the invention, as expressed in linear resistivity, is less than about 20 Ohm.cm, and preferably, ranging between several Ohm.cm and 20 Ohm.cm. The electrically conductive liquid media can be constituted by an aqueous or non-aqueous electrolyte. A suitable aqueous electrolyte is water containing ionizable compounds, notably salts such as halogenide salts, for example NaCl, $NH_4Cl$, sulfates or nitrates with alkaline or alkaline earth metals or transition metals such as copper. A currently preferred electrically conductive aqueous liquid medium is constituted by water salted at the rate of 100 or 200 g/l and having a linear resistivity value of 10 and 5 Ohm.cm. Suitable non-aqueous conductive liquid media are the conductive oils, rendered conductive by the addition of conductive particles such as metallic particles, which are well known to of anyone skilled in the art.

According to a second aspect of the present invention a device, is also provided, for improving the rate of electrical discharge produced in a liquid medium such as water, between at least two discharge electrodes fed intermittently with electric current, which device comprises means for reducing the resistance to the passage of the current at least between the electrodes so as to bring it to a resistance value approximately equal to the critical resistance.

According to a particularly advantageous embodiment, said means for reducing the electrical resistance to the passage of the electric current comprises an electrically conductive liquid medium interposed at least between the electrodes. Said interposition may be achieved by immersing the electrodes in said electrically conductive medium or by injecting an electrically conductive medium at the level of the electrodes.

Other characteristics of the electrically conductive medium according to the invention have been described with reference to the method and are, understandably, also applicable to the device.

According to the invention, the discharge is produced through an electrically conductive medium, thus eliminating substantially completely the latency time. Moreover, a considerable increase of the reproducibility of the pressure wave generated between the electrodes is obtained, while the oscillations associated with the formation of an arc are prevented. This is mainly due to the fact that in the conventional case, an arc is ignited at random in time and in space, inducing the formation of an inaccurately localized steam bubble, which is not the case according to the present invention. Therefore, according to the invention, the presence of an oscillating current is eliminated, so that the discharge is of the critically damped type, as will be more readily understood from the description given with reference to the appended drawing.

Also according to the invention, the energy is supplied more suddenly (critical rate) so that the pressure generated is higher for the same value of discharge voltage of the capacitor.

The invention therefore provides all the technical advantage indicated hereinabove, which were unexpected and non-obvious to anyone skilled in the art.

Other aims, characteristics and advantages of the invention will appear more clearly in light of the following description made with reference to the accompanying drawings which show the presently preferred embodiment of the device, given by way of example and non-restrictively.

BRIEF DESCRIPTION OF THE DRAWINGS

FIG. 2 therefore illustrates diagrammatically, in partial cross-section, a truncated ellipsoidal reflector or the type described in RIEBER's U.S. Pat. No. 2,559,227, according to a cross-sectional plane passing through the electrodes and the internal focus point of the truncated ellipsoidal reflector, with the capacitor charge and discharge circuit between the electrodes, a resistor R being provided in parallel to the capacitor.

FIGS. 3*a*, 3*b*, 3*c* respectively illustrate, similarly to FIGS. 1*a*, 1*b*, 1*c* the curves of voltage, current and energy obtained according to the present invention, an electrically conductive liquid medium being interposed at least between the electrodes.

DETAILED DESCRIPTION OF PREFERRED EMBODIMENTS

Figure 1A:
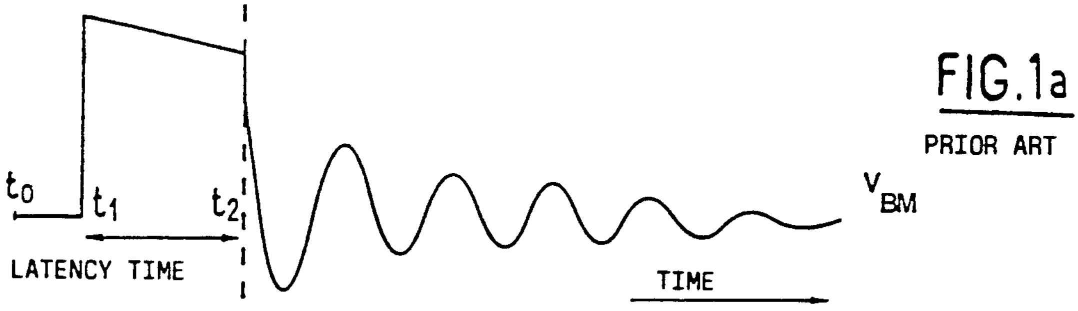
FIG. 1a PRIOR ART
FIGS. 1*a*, 1*b* and 1*c* respectively show the curves of voltage, current and energy during the conventional discharge of an electric arc generated between two electrodes using a discharge circuit according to U.S. Pat. No. 2,559,227 of RIEBER, diagrammatically illustrated in FIG. 2.

With reference to FIG. 2, a truncated ellipsoidal reflector, of the type described in RIEBER's U.S. Pat. No. 2,559,227, included herein by way of reference, is diagrammatically illustrated and designated by the general reference 10, said reflector being provided with two discharge electrodes 12, 14 which are diametrically opposed and converge towards the internal focus point symbolized by reference F. The second focal point of the ellipsoid is situated outside the truncated ellipsoidal reflector 10 and it is with that second focus point that the target to be destroyed will be made to coincide, as described in detail in RIEBER's U.S. patent. Said target, of course, can be constituted by a concretion. The electrode 12 is, for example, grounded, as illustrated in the figure, and connected also to one side of a capacitor C. The other electrode 14 is connected to the capacitor C via a switching device I, such as for example a gas discharge arrester, which is intermittently switched off by a control symbolically designated by reference 20. A high value resistor R is provided in parallel to capacitor C. The capacitor C is charged with a high voltage, between 10,000 and 20,000 V, from a source of power as described for example in FIG. 1 of commonly assigned document EP-A-0 296 912 equivalent to U.S. Pat. No. 4,962,753, included herein by way of reference, the corresponding circuit not being illustrated for comprehension's sake. Usually, the ellipsoidal reflector 10 is filled with a shockwave transmitting liquid, normally water, whose resistance to the passage of an electrical current is not inconsiderable. Said electrical resistance value of normally ionized water, as expressed in linear resistivity value, is in average about 1500 Ohm.cm. In the case of oils, which are very insulating, such as in the case of RIEBER's U.S. Pat. No. 2,559,227, the linear resistivity value is about 3 to 5 M.Ohm.cm.

Figure 1B:
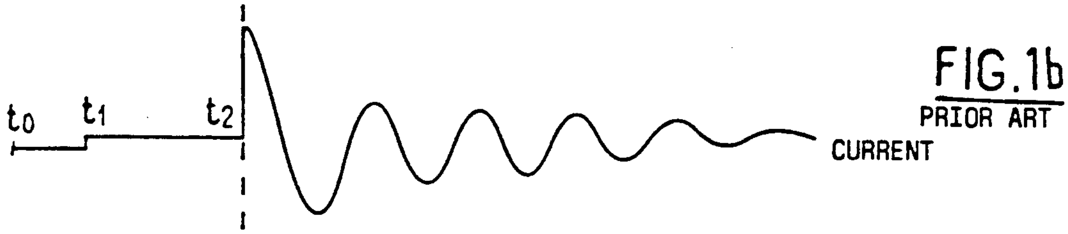
FIG. 1b PRIOR ART
Figure 1C:
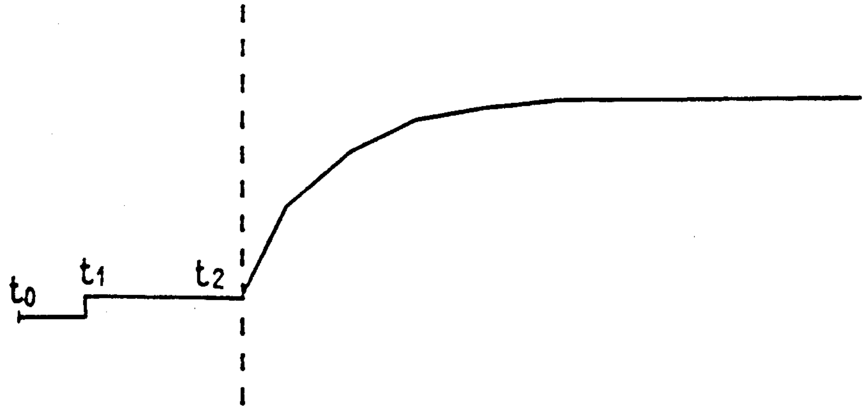
FIG. 1c PRIOR ART

When producing an electric discharge in a circuit such as that illustrated in FIG. 2, where the liquid medium between the electrodes 12, 14 is constituted by normally ionized water, a discharge chronogram is obtained such as illustrated in FIGS. 1*a*, 1*b* and 1*c* for which there is a not inconsiderable latency time while the discharge rate is of the oscillatory type, associated to the formation of an arc, this delivering the energy progressively to the external medium.

According to the present invention, means are used for considerably reducing the resistance to the passage of the current at least between the electrodes, bringing it to a resistance value near to or slightly higher than the critical resistance, this constituting a solution which is quite the opposite to that recommended in Applicants' document EP-A-0 296 912 which proposes on the contrary to considerably increase the electrical resistance between the electrodes by interposing an insulating element between them, and which is even the opposite of what is proposed in U.S. Pat. No. 3,559,435 of GERBER.

According to the invention, said means for reducing the electrical resistance preferably comprise an electrically conducting liquid medium which is interposed at least partly between the electrodes. In practice, this can be achieved very easily by immersing the electrodes in said electrically conducting medium, i.e. in the case of hydraulic pressure wave generation, by filling the ellipsoidal reflector 10 with said electrically conductive liquid medium.

According to an advantageous embodiment of the invention, the electrically conducting liquid media have an electrical resistance which is at least 1/10 and preferably 1/100 of the value of the electrical resistance of normally ionized water, used as reference, and which is normally of 1500 Ohm.cm as expressed in linear conductivity. preferably, the electrical resistance of the electrically conductive medium according to the invention, as expressed in linear conductance, is less than about 20 Ohm.cm, better still it ranges between several Ohm.cm and 20 Ohm.cm. Thus, the volume between the electrodes has a resistance equal or very near to the critical resistance (which is generally between 0.3 Ohm and several Ohms). Consequently, the current traverses the conductive liquid, heats it for as short a time as possible, in view of the value of the external parameters, as the capacitance C of condensation and the inductance L of the discharge circuit, a pressure wave generating bubble of gas if formed in the near-total absence of plasma.

Any aqueous or non-aqueous electrically conductive liquid can be used as an electrically conductive medium according to the present invention. A suitable aqueous electrically conductive liquid is an aqueous electrolyte constituted from pure water to which ionizable soluble compounds are added, such as salts like halogenides, in particular chlorides, sulfates, nitrates. A particularly preferred aqueous electrolyte is water with addition of NaCl or of $NH_4Cl$. The medium given more preference is water salted at 100 or 200 g/l whose respective linear resistivity is from 10 to 5 Ohm.cm. Among suitable non-aqueous electrolytes are electrically conductive oils, namely oils rendered conductive by addition of electrically conductive particles, such as metallic particles.

According to the invention, when using an electrically conductive medium, a discharge chronogram is obtained, such as illustrated in FIGS. 3*a*, 3*b*, 3*c*. It is found that, as soon as the electrodes are charged at time $t_1$, the discharge of capacitor C is quasi-instantaneous. Moreover, the discharge is of the critically type, and is no longer sinusoidal. Also, the energy is delivered to the external medium for a much shorter time than in the case of an oscillating rate, or in the case of prior rates with latency times, thus increasing the value of the pressure wave generated in a shorter time.

The result is a considerable increase of the reproducibility of the pressure wave owing to the fact that the discharge is no longer ignited at random in time and in space, but on the contrary at time $t_1$ and induces the formation of a perfectly localized steam bubble. The chronogram shown in FIG. 3 was obtained, by using water salted at 200 g/l as the electrically conductive medium for immersing the electrodes 12, 14, as well as a capacitor having a capacitance of 100 nF, with a spacing between the electrodes of 0.4 mm, the discharge circuit of FIG. 2 having a total self inductance L of 80 nH.

In the description and claims, it will be recalled that the critical resistance is the value of the resistance between the electrodes for which the relation:

$$R_c = \sqrt{\frac{L}{C}}$$

is substantially met. In the formula L is the value of internal self-inductance of the discharge circuit of capacitor C, and C is the capacitance value of the capacitor.

It will be noted that according to the invention, using an electrically conductive liquid medium, an excellent reproducibility of the pressure waves is obtained, the mean deviation being less than 5%, particularly if salted water is used, whereas said means deviation is about 30% if normally ionized water is used. The invention therefore provides all the aforesaid non-obvious and unexpected technical advantages and as a result solves all the aforesaid technical problems. The invention also provides the possibility of implementing the aforedescribed method.

Finally, the invention also covers an apparatus generating pressure waves by generating an electric current between two electrodes, characterized in that it uses a method or device for improving the discharge rate such as described hereinabove. In particular, said apparatus for generating pressure waves is characterized in that it comprises a truncated ellipsoidal reflector filled with an electrically conductive liquid medium according to the invention.

Said apparatus is preferably applied to the extracorporeal destruction of concretions by pressure waves (kidney lithiases, cholelithiases, urinary calculi) or of tissues (such as tumors) or to the treatment of bone fractures.

What is claimed is:

1. Method for improving the reproducibility of electric discharge produced in a liquid medium, such as water, for producing shockwaves, comprising the steps of:

providing in said liquid medium two closely-spaced discharge electrodes fed intermittently with electric current for producing a punctual type discharge therebetween;

sufficiently reducing the electrical resistance of the liquid medium, at least between said electrodes, to prevent any substantial discharge oscillation and to substantially completely eliminate a discharge latency time.

2. Method as claimed in claim 1, wherein said step of reducing the electrical resistance in said liquid medium comprises using an electrically conducting liquid medium at least between said electrodes.

3. Method as claimed in claim 2, wherein the resistance of said electrically conductive liquid medium is no greater than about 1/10 of the value of the resistance of normally ionized water.

4. Method as claimed in claim 3, wherein the electrical resistance expressed in terms of electrical resistivity of said electrically conductive liquid medium is in the range of about 3 Ohms.cm to about 20 Ohms.cm.

5. The method of claim 1, further comprising the step of providing a truncated ellipsoidal reflector filled with said liquid medium.

6. The method of claim 5, further comprising the steps of disposing said electrodes for discharge substantially at one focus of said truncated ellipsoidal reflector for impacting a desired portion of a subject disposed at a second focus of said truncated ellipsoidal reflector disposed outside thereof, whereby said portion of said subject is treated by said shockwaves concentrating at said second focus.

7. Method as claimed in claim 1, wherein the electrical resistance of said electrically conductive liquid medium is no greater than about 1/100 of the value of the resistance of normally ionized water.

8. Method for improving the reproducibility of electric discharge produced in a liquid medium, such as water, for producing shockwaves, comprising the steps of: providing in said liquid medium two closely-spaced electrodes fed intermittently with electric current for producing a punctual type discharge therebetween; wherein the electrical resistance expressed in terms of electrical resistivity of said electrically conductive liquid medium is less than about 20 Ohm.cm.

9. A method as in claim 8, wherein the resistance of said electrically conductive liquid medium is no greater than about 1.10 of the value of the resistance of normally ionized water.

10. A device for generating shockwaves of the type including a housing containing a liquid medium and having two electrodes disposed in said liquid medium, the device further comprising:

means for intermittently feeding said electrodes with electric current for providing shockwaves between said electrodes, said electrodes being sufficiently closely spaced for producing a punctual type discharge therebetween; and means for sufficiently reducing the electrical resistance at least between the electrodes to prevent any substantial discharge oscillation and to substantially completely eliminate discharge latency time.

11. Device as claimed in claim 10, wherein said means for reducing the electrical resistance between said electrodes comprises an electrically conductive liquid medium interposed between the electrodes.

12. Device as claimed in claim 11, wherein the electrically conductive liquid medium is constituted by an aqueous electrolyte prepared from pure water to which an ionizable compound selected from the group consisting of halogenide salts, sulfates and nitrates, has been added.

13. Device as claimed in claim 11, wherein the electrically conductive liquid medium is constituted by an aqueous electrolyte prepared from pure water to which ionizable compounds have been added.

14. Device as claimed in claim 11, wherein the electrically conductive liquid medium has an electrical resistance expressed in terms of electrical resistivity lower than about 20 Ohm.cm, and said conductive liquid medium is water salted at about 200 g/l.

15. Device as claimed in claim 10, wherein said electrically conductive liquid medium has an electrical resistance, measured in terms of linear resistivity, which is no greater than about 1/10 of the value of the resistance of normally ionized water.

16. Device as claimed in claim 15, wherein the electrically conductive medium is constituted by an aqueous or non-aqueous electrolyte.

17. Device as claimed in claim 10, wherein said electrically conductive liquid medium has an electrical resistance, measured in terms of linear resistivity, which is no greater than about 1/100 of the value of the resistance of normally ionized water.

18. The apparatus of claim 10, wherein said housing comprises a truncated ellipsoidal reflector.

19. The apparatus of claim 18, wherein said electrodes are substantially disposed at one focus of said truncated ellipsoidal reflector for impacting a desired portion of a subject disposed at a second focus of said truncated ellipsoidal reflector, whereby said portion of said subject is treated by said shockwaves concentrating at said second focus.

20. Device for generating shockwaves of the type including a housing containing a liquid medium and having two electrodes disposed in said liquid medium, the device further comprising:

means for intermittently feeding said electrodes with electric current for providing shockwaves between said electrodes, said electrodes being sufficiently closely spaced for producing a punctual type discharge therebetween;

wherein said means for reducing the electrical resistance between said electrodes comprises an electrically conductive liquid medium interposed between the electrodes; and wherein the electrically conductive medium has an electrical resistance, expressed in terms of linear resistivity, lower than about 20 Ohm.cm.

21. Device as in claim 20, wherein said liquid medium is water salted at about 100 to about 200 g/l.

* * * * *

UNITED STATES PATENT AND TRADEMARK OFFICE
CERTIFICATE OF CORRECTION

PATENT NO. : 5,105,801
DATED : April 21, 1992
INVENTOR(S) : Cathignol et al.

It is certified that error appears in the above-identified patent and that said Letters Patent is hereby corrected as shown below:

Column 5, line 10, change "or" to --of--.

Column 6, line 63, after "critically" insert --damped--.

<u>In the Claims</u>:

Col. 8, Claim 9, line 34, change "1.10" to --1/10--.

Signed and Sealed this

Twentieth Day of July, 1993

Attest:

Michael K. Kirk

MICHAEL K. KIRK

*Attesting Officer*

*Acting Commissioner of Patents and Trademarks*